United States Patent [19]

Cook

[11] 4,130,710
[45] Dec. 19, 1978

[54] PIPERIDINE DERIVATIVES

[75] Inventor: Barry Cook, Flixton, England

[73] Assignee: Ciba-Geigy Corporation, Ardsley, N.Y.

[21] Appl. No.: 679,530

[22] Filed: Apr. 23, 1976

Related U.S. Application Data

[62] Division of Ser. No. 380,041, Jul. 17, 1973, Pat. No. 3,971,795.

[30] Foreign Application Priority Data

Jul. 28, 1972 [GB] United Kingdom ............... 35486/72

[51] Int. Cl.$^2$ ........................................... C07D 211/32
[52] U.S. Cl. .................. 542/418; 260/244.4; 542/438; 542/421; 542/429; 546/16; 546/190; 546/187; 546/208; 546/233; 546/234; 546/247; 546/203; 546/205; 544/130; 260/45.8 N

[58] Field of Search ..................... 260/240 J, 247.2 A, 260/293.63, 293.64, 293.71, 293.73, 293.76, 293.77, 293.85, 293.86, 247.7 V, 293.69; 252/403; 542/418, 438, 421, 429; 544/130

[56] References Cited

U.S. PATENT DOCUMENTS

| 2,556,516 | 6/1951 | Brooker et al. | 542/421 |
| 3,436,369 | 4/1969 | Kitaoka et al. | 260/45.8 |
| 3,850,877 | 11/1974 | Cook | 260/45.8 N |

FOREIGN PATENT DOCUMENTS

46-31734 9/1971 Japan.

*Primary Examiner*—John M. Ford
*Attorney, Agent, or Firm*—Vincent J. Cavalieri

[57] ABSTRACT

New piperidine derivatives and in particular esters and amides of substituted (piperidinylidene-4) acetic acid are used as stabilizers for polymers, especially for polyolefines.

19 Claims, No Drawings

PIPERIDINE DERIVATIVES

This is a divisional of application Ser. No. 380,041 filed on July 17, 1973 now U.S. Pat. No. 3,971,795.

In Japanese Patent Application No. 71.31734 there are disclosed compounds having the formula:

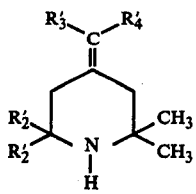

wherein $R'_1$ and $R'_2$ are each an alkyl group or together they form a C5-C7 saturated alicyclic residue or a group having the formula:

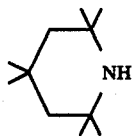

and $R'_3$ and $R'_4$ are each CN, aryl, alkoxy, carbonylacyl or carbamoyl; or salts of these compounds. The compounds and their salts are recommended as light stabilisers for polyolefins.

We have found that certain novel N-substituted piperidinylidene derivatives, related to these known compounds, also have utility as stabilisers for polymers.

The present invention provides a compound having the formula:

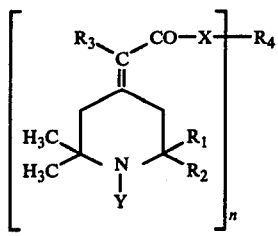

wherein n is 1, 2, 3 or 4, Y is hydrogen or a straight- or branched alkyl residue having from 1 to 12 carbon atoms, an alkenyl residue having from 3 to 12 carbpon atoms or an aralkyl residue having from 7 to 12 carbon atoms and $R_1$ and $R_2$ are the same or different and each is a straight- or branched alkyl residue havng from 1 to 12 carbom atoms, or $R_1$ and $R_2$ together with the carbon atom to which they are attached form a cycloalkyl group having from 5 to 12 carbon atoms; $R_3$ is hydrogen, a straight- or branched alkyl residue having from 1 to 4 carbon atoms, an aralkyl residue having from 7 to 12 carbon atoms, a cycloalkyl group having 5 or 6 carbon atoms, $R_4$ is a hydrocarbyl residue having from 1 to 20 carbon atoms being either unsubstituted or substituted by halogen, or interrupted by one of more oxygen or sulfur atoms or $R_4$ is a metal ion, or, when n is 1, $R_4$, in addition, is hydrogen or has the structure:

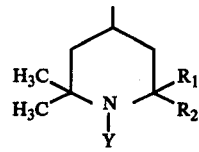

wherein Y, $R_1$ and $R_2$ have their previous significance, X is —O—, —S— or >$NR_5$ wherein $R_5$ has the same significance as $R_3$ or when n is 1 in addition $R_5$ and $R_4$, together with the nitrogen atom to which they are bound form a heterocyclic residue having from 4 to 10 carbon atoms; as well as salts of the amine function of the compound of formula I.

When n is 1, $R_4$ can be for instance, hydrogen, a monovalent straight or branched aliphatic residue (either saturated or unsaturated) having from 1 to 20 carbon atoms, an alicyclic residue having from 5 to 20 carbon atoms, an aryl residue having from 6 to 15 carbon atoms, or $R_4$ and $R_5$ together with the nitrogen atom to which they are bound form a heterocyclic residue having from 4 to 10 carbon atoms and optionally having one other heteroatom.

Examples of the group $R_4$ when n is 1, apart from hydrogen are: methyl, ethyl, n-propyl, isopropyl; n-butyl, sec-butyl, t-butyl, n-pentyl, neopentyl, 2-ethylpropyl, 2-methylbutyl, n-hexyl, n-octyl, t-octyl, n-dodecyl, n-octadecyl, eicosyl, 2-methoxyethyl, 3-chloropropyl, 2-methylthioethyl, α-methallyl, dec-9-enyl, heptadec-8-enyl, oleyl crotyl, cinnamyl, propargyl, 2,4-hexdienyl, benzyl α-methylbenzyl, α,p-dimethylbenzyl, diphenylmethyl, 2-chlorobenzyl, cyclopentyl, cyclohexyl, cyclooctyl, 4-methylcyclohexyl, cyclododecyl, 4-chlorocyclohexyl, 9-fluorenyl, adamantyl, phenyl, 4-methylphenyl, 4-t-octylphenyl, 4-methoxyphenyl, α-naphthyl, 4-biphenyl, 2-fluorenyl, or the group:

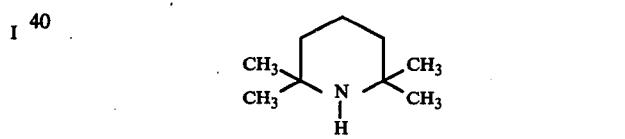

Examples of structures where $R_4$ and $R_5$ form a ring system, together with the nitrogen to which they are bound are 1-pyrrolidinyl, 1-piperidinyl and 1-morpholinyl.

When n is 2, $R_4$ may be a divalent straight or branched aliphatic residue (either saturated or unsaturated) having from 2 to 20 carbon atoms, a divalent alicyclic residue having from 5 to 20 carbon atoms, a divalent alalkyl residue having from 8 to 20 carbon atoms or a divalent aryl residue having from 6 to 20 carbon atoms.

When n is 2, examples of the group $R_4$ are 1,2-ethylene, 1,3-n-propylene, 1,4-n-butylene, 1,3-n-butylene, 1,6-n-hexylene, 1,7-n-heptylene, 1,10-n-decylene, 2,2-dimethyl-1,3-propylene, 1,2,4-trimethyl-1,4-butylene, 3-thia-1,5-pentylene, 3-oxa-1,5-pentylene, 1,4-but-2-enylene, 1,4-but-2-ynylene, 2,5-hex-3-enylene, 1,2-cyclohexylene, 1,3-cyclohexylene, 1,4-cyclohexylene, hexahydro-p-xylylene, p-xylylene, m-xylylene, 1,2-phenylene, 1,4-phenylene, 2,2'-biphenylene, 4,4'-biphenylene, 2,6-naphthylene, and 2,7-fluorenylene.

When n is 3, $R_4$ may be a trivalent straight or branched chain aliphatic residue (either saturated or unsaturated) having from 3 to 15 carbon atoms, a trivalent alicyclic residue having from 5 to 15 carbon atoms, a trivalent aralkyl residue having from 9 to 15 carbon atoms, or a trivalent aryl residue having from 6 to 15 carbon atoms, such as 1,2,3-trisubstituted propane, 1,2,4-trisubstituted butane, 2,5-dimethyl-1,2,6-trisubstituted cyclohexane, 1,3,5-tri substituted cyclohexane and 1,2,7-trisubstituted anthracene.

When n is 4, $R_4$ may be a straight or branched chain tetravelent aliphatic residue (either saturated or unsaturated having from 4 to 12 carbon atoms or a tetravalent alicyclic having from 5 to 12 carbon atoms, such as tetramethylene methane and 1,1,4,4-tetramethylene cyclohexane.

When $R_4$ is an aliphatic, alicyclic, aryl or aralkyl residue, each of these residues may be unsubstituted or substituted by halogen or interrupted by one or more oxygen or sulphur atoms.

Of the compounds of formula I in which $R_4$ is an aliphatic residue, those are preferred, for reasons of superior volatility and compatibility, in which $R_4$ is higher aliphatic residue, that is a residue having at least 5 carbon atoms. Moreover, within this sub-group of preferred compounds, particular preference is given to those members in which $R_4$ is a di-, tri- or tetravalent residue.

When $R_4$ is a metal ion, it is preferably a transitional metal ion, more preferably an ion of a metal of Group VIII of the Periodic System of Elements and especially an ion of nickel.

Examples of Y, in the compound of formula I are, hydrogen, methyl, ethyl, n-propyl, isopropyl, n-butyl, sec-butyl, n-hexyl, n-octyl, n-dodecyl, allyl, α-methallyl, 10-undecenyl, benzyl, α-methylbenzyl, p-methylbenzyl, α,p-dimethylbenzyl, α-naphthylmethyl.

Particularly preferred substituents Y are hydrogen and straight or branched alkyl groups having from 1 to 4 carbon atoms and the most preferred values for Y are hydrogen and methyl.

Examples of the groups $R_1$ and $R_2$ are methyl, ethyl, n-propyl, isopropyl, n-butyl, sec-butyl; n-hexyl, n-dodecyl, or together with the carbon to which they are bound $R_1$ and $R_2$ can form a group such as:

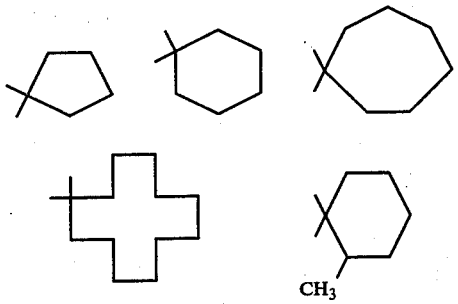

Particularly preferred substituents $R_1$ and $R_2$ are straight or branched alkyl groups hving 1 to 4 carbon atoms and the most preferred value for each of $R_1$ and $R_2$ is methyl.

Examples of the groups $R_3$ and $R_5$ are hydrogen, methyl ethyl, n-propyl, isopropyl, n-butyl, sec-butyl, benzyl, a-methylbenzyl, α,p-dimethylbenzyl, cyclohexyl, cyclopentyl.

Particularly preferred substituents $R_3$ and $R_5$ are hydrogen or alkyl having frm 1 to 4 carbon atoms and the most preferred is hydrogen.

Examples of salts of the amine function of compounds of formula I that can be used according to the invention include salts of an inorganic acid, such a phosphates, carbonates, sulphates, chlorides and the like, as well as organic acid salts such as acetates, stearates, maleates, citrates, tartrates, oxalates, and benzoates, and the substituted carbamic acids.

Examples of the esters and amides of formula I are given in the following list:

(2,2,6,6-Tetramethylpiperidinylidene-4)acetic acid
Ethyl (2,2,6,6-tetramethylpiperidinylidene-4)acetate
2'-Methoxyethyl(2,2,6,6-tetramethylpiperidinylidene-4)acetate
2'-Methylthioethyl(2,2,6,6-tetramethylpiperidinylidene-4)acetate
Cyclohexy(2,2,6,6-tetramethylpiperidinylidene-4)acetate
4'-Chlorocyclohexyl(2,2,6,6-tetramethylpiperidinylidene-4)acetate
n-Octyl(2,2,6,6-tetramethylpiperidinylidene-4)acetate
2-Octyl(2,2,6,6-tetramethylpiperidinylidene-4)acetate
n-Octadecyl(2,2,6,6-tetramethylpiperidinyldene-4)acetate
Benzyl(2,2,6,6-tetramethylpiperidinylidene-4)acetate
4'-methoxylbenzyl(2,2,6,6-tetramethylpiperidinylidene-4)acetate
Phenyl(2,2,6,6-tetramethylpiperidinylidene-4)acetate
2-chlorophenyl(2,2,6,6-tetramethylpiperidinylidene-4)acetate
(2',2',6',6'-tetramethylpiperidinyl-4'-) (2,2,6,6-tetramethyl-piperidinylidene-4)acetate
(2,2,6,6-tetramethylpiperidinylidene-4)acetate
Crotyl(2,2,6,6-tetramethylpiperidinylidene-4)acetate
Cinnamyl(2,2,6,6-tetramethylpiperidinylidene-4)acetate
1,2,2,6,6-(Pentamethylpiperidinylidene-4)acetic acid
Ethyl(1,2,2,6,6-Pentamethylpiperidinylidene-4)acetate
2'-Ethoxyethyl(1,2,2,6,6-Pentamethylpiperidinylidene-4)acetate
n-Octyl(1,2,2,6,6-Pentamethylpiperidinylidene-4)acetate
2-Octyl(1,2,2,6,6-Pentamethylpiperidinylidene-4)acetate
Cyclohexyl(1,2,2,6,6-Pentamethylpiperidinylidene-4)acetate
n-Dodecyl(1,2,2,6,6,-pentamethylpiperidinyldene-4)acetate
Benzyl(1,2,2,6,6-Pentamethylpiperidinylidene-4)acetate
Phenyl(1,2,2,6,6-Pentamethylpiperidinylidene-4)acetate
Allyl(1,2,2,6,6-Pentamethylpiperidinylidene-4)acetate
α-(n-Butyl)ethyl(2,2,6,6-tetramethylpiperidinylidene-4)acetate
N-n-Hexyl(2,2,6,6-tetramethylpiperidinylidene-4)acetamide
N(n-Dodecyl)(2,2,6,6-tetramethylpiperidinylidene-4)acetamide
N(n-Octadecyl)(2,2,6,6,-tetramethylpiperidinylidene-4)acetamide
N-Cyclohexyl(2,2,6,6-tetramethylpiperidinylidene-4)acetamide N-Benzyl(2,2,6,6-tetramethylpiperidinylidene-4)acetamide
N-phenyl(2,2,6,6,-tetramethylpiperidinyldene-4)acetamide
N-(4'-Chlorophenyl)(2,2,6,6-tetramethylpiperidinylidene-4)acetamide
N-Allyl(2,2,6,6-tetramethylpiperidinylidene-4)acetamide
(2,2,6,6-tetramethylpiperidinylidene-4)acetamide
(1,2,2,6,6-pentamethylpiperidinylidene-4)acetamide
N-(n-Hexyl) (1,2,2,6,6-pentamethylpiperidinylidene-4)acetamide
N-(n-Decyl) (1,2,2,6,6-pentamethylpiperidinylidene-4)acetamide
N-Cyclohexyl(1,2,2,6,6-pentamethylpiperidinylidene-4)acetamide
N-Benzyl(1,2,2,6,6-pentamethylpiperidinylidene-4)acetamide
N-Phenyl(1,2,2,6,6-pentamethylpiperidinylidene-4)acetamide
N-Crotyl(1,2,2,6,6-pentamethylpiperidinylidene-4)acetamide
α-(n-Butyl)-N-hexyl(2,2,6,6-tetramethylpiperidinylidene-4)acetamide
α-Methyl-M-cyclohexyl(1,2,2,6,6-pentamethylpiperidinylidene-4)acetamide
N,N'-Di[(2,2,6,6-tetramethylpiperidinylidene-4)acetyl]hexamethylenediamine
N,N'-Di[(2,2,6,6-tetramethylpiperidinylidene-4)acetyl]ethylene diamine
N,N'-Di[(1,2,2,6,6-pentamethylpiperidinylidene-4)acetyl]ethylene diamine
1-[(2,2,6,6-tetramethylpiperidinylidene-4)acetyl]morpholine
Ethyl(1-n-butyl-2,2,6,6-tetramethylpiperidinylidene-4)acetate
Cyclohexyl(1-benzyl-2,2,6,6-tetramethylpiperidinylidene-4)acetate
N-n-Dodecyl(1-allyl-2,2,6,6-tetramethylpiperidinylidene-4)acetamide
n-Butyl(2,2-dimethyl-6,6-dipropylpiperidinylidene-4)acetate
Octadecyl(2,2,6, -trimethyl-6-butylpiperidinylidene-4acetate
2-Octyl(1-n-butyl-2,2-dimethyl-6,6-diisopropyl-piperidinylidene-4)acetate
Ethyl(1-aza-2,2-dimethylspiro[5,5]-undecylidene-4)acetate
1,2-Ethylene-di[2',2',6',6'-tetramethylpiperidylidene-4')acetate]
1,2-Ethylene-di[1',2',2',6', 6'pentamethylpiperidinylidene-4')acetate]
1,4-Butylene-di[(2',2',6',6'-tetramethylpiperidinylidene-4')acetate]
1,4-Butylene-di[(1',2',2',6',6'-pentamethylpiperidylidene-4')]acetate
3-Thia-1,5-pentylene-di[(2',2',6',6'-tetramethyl-piperidinylidene-4')acetate]
Ethyl-tris[(2,2,6,6-tetramethylpiperidinylidene-4)acetoxymethyl]methane
Tetrakis[(2,2,6,6-tetramethylpiperidinylidene-4)acetoxymethyl]methane
Tetrakis[(1,2,2,6,6-pentamethylpiperidinylidene-4)acetoxymethyl]methane
Ethyl(2,2,6,6-tetramethylpiperidinylidene-4)thioacetate
n-Octyl(2,2,6,6-tetramethylpiperidinylidene-4)thioacetate
n-Octadecyl(2,2,6,6-tetramethylpiperidinylidene-4)thioacetate
Cyclohexyl(2,2,6,6-tetramethylpiperidinylidene-4)thioacetate
Cyclohexyl(1,2,2,6,6-pentamethylpiperidinylidene-4)thioacetate
n-Butyl(1,2,2,6,6-pentamethylpiperidinylidene-4)thioacetate
1,4-Butylene-di[(2',2',6',6'-tetramethylpiperidinylidene-4')thioacetate]
1,2-Ethylene-di[(1',2',2',6',6'-tetramethylpiperidinylidene-4')thioacetate]
Benzyl(2,2,6,6-tetramethylpiperidinylidene-4)thioacetate
Phenyl(2,2,6,6-tetramethylpiperidinylidene-4)thioacetate
Benzyl(1,2,2,6,6-pentamethylpiperidinylidene-4)thioacetate
Octyl(1-ethyl-2,2,6,6-tetramethylpiperidinyl-4)thioacetate
Bis[(2,2,6,6-tetramethylpiperidinylidene-4)acetato]-Nickel$^{II}$
3,5,5-Trimethyl-1-[(2',2',6',6'-tetramethylpiperidinylidene-4')acetamido]-3[(2'',2'',6'',6''-tetramethyl-piperidinylidene-4'')acetamidomethylene]cyclohexane
1,12-Dodecylene-di-[(2',2',6',6'-tetramethyl-piperidinylidene-4')acetate]

The present invention also provides a first preferred process in which a compound of formula I is produced comprising reacting a compound having the formula:

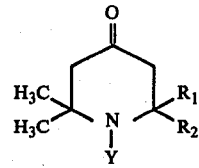

wherein $R_1$, $R_2$ and Y have their previous significance, with a compound having the formula:

$$(R_7O)_2 \overset{O}{P}(O)_C^- R_3CO.OR_6 \ ^+B \qquad III$$

wherein $R_3$ has its previous significance, $R_6$ and $R_7$ are the same or different and each is an alkyl group having from 1 to 4 carbon atoms and $B^+$ is an organic or inorganic base cation, preferably an alkali metal cation, to give a compound having the formula:

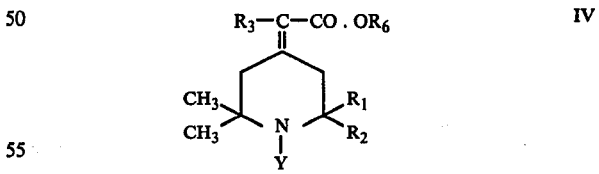

which is then reacted with a compound having the formula:

$$R_4(XH)_n \qquad V$$

wherein $R_4$, X and n have their previous significance.

The first reaction stage may be conveniently effected in a solvent inert, under the reaction conditions, to the reactants and the reaction products, for instance benzene, cyclohexane, toluene, dioxan or ethanol; the reaction may be carried out at an ambient temperature but is preferably effected at the reflux temperature of the solvent used.

The second reaction may be carried out with or without a solvent, inert under the reaction conditions to the reactants and the reaction products and with or without a catalyst for instance lithium amide, alkali metal alkoxides, p-toluene sulphonic acid, calcium hydroxide, tetra-n-butyl titanate or dibutyl-tin oxide. The temperature employed can be in a range from room temperature to 200° C., preferably in the range of from 140°–180° C.

The starting-materials of formulae II, III and V are known compounds which may be produced by methods well-known per se.

In a modification of the first process according to the invention, the compound of formula Ii may be reacted with a compound having the formula:

wherein $R_3$, $R_4$, $R_7$, X and B have their previous significance, to give a compound of formula I but restricted to those compounds wherein n is 1.

In a less preferred process according to the present invention, a compound of formula I is produced by reacting a compound having the formula:

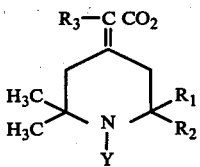

VI wherein $R_1$, $R_2$ and $R_3$ have their previous significance and Z is halogen with a compound of formula V as hereinbefore defined.

The reaction is conveniently effected in a solvent inert under the reaction conditions to the reactants and the reaction products. Suitable solvents include benzene, toluene, cyclohexane and dioxan. Advantageously, the reaction is conducted at an elevated temperature preferably at the reflux temperature of the reaction mixture.

The starting-material of formula VI may be produced for example from the comound of formula IV by methods well-known per se.

An alternative method of prepartion of compounds of formula I is by the reaction of a compound having the formula:

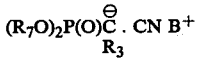

VII wherein $R_3$, $R_7$ and B have their previous significance, with a compound of formula II as hereinbefore defined, to give a compound of formula VIII:

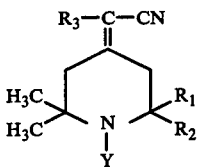

VIII wherein $R_1$, $R_2$, $R_3$ and Y have their previous significance followed by hydrolysis or alcoholysis to give a compound of formula:

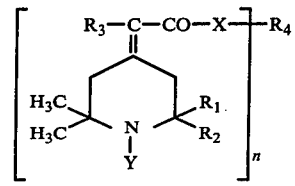

wherein $R_1, R_2, R_3, R_4$, and Y have their previous significance, n is 1 and X is NH or 0.

In general, the compounds of formula I may be extracted from the crude reaction mixture by conventional techniques such as solvent extraction. If desired, the compounds of formula I so obtained may be further purified for instance by distillation, preferably under reduced pressure, or by recrystallisation from a suitable solvent.

In the processes according to the present invention, instead of using starting-materials of formulae II and VI which contain the grouping >N—Y, the corresponding >N—H compounds may be used as starting-material, the group Y being introduced into the molecule during a subsequent reaction stage. Thus, if Y is an alkyl, alkenyl or aralkyl group, these groups may be introduced at the nitrogen atom by reacting the >NH compound with an alkyl, alkenyl or aralkyl halide or by a Leuckart or Wallach reaction using the corresponding aldehyde or ketone.

Salts of the amine function of the compounds of formula I may be prepared by the reaction of the appropriate acid with a solution of a compound of formula I in an inert solvent.

Metal salts of formula I may be prepared by reaction of a compound having the formula:

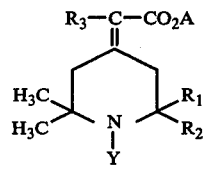

wherein $R_1$, $R_2$, $R_3$ and Y have their previous significance and A is an alkali metal ion, preferably sodium, with a compound having the formula:
$M(Z)_n$ wherein M is a metal ion, preferably a transition metal ion, especially nickel, Z is halogen and n is 1,2,3 or 4.

The reaction is conveniently effected in a solvent, for instance, ethyl alcohol or water.

The present invention further provides a composition comprising an organic material and, as stabiliser, a minor proportion of a compound of formula I as hereinbefore defined.

Compounds of formula I have been found to impart to polyolefines and exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation especially for low- and high-density polyethylene and polypropylene and polystyrene as well as polymers of butene-1, pentene-1, 3-methylbutene-1, hexene-1, 4-methylpentene-1, 4-methylhexene-1 and 4,4-dimethylpentene-1, and also co- and ter-polymers of olefines, particularly of ethylene or propylene.

Other organic materials susceptible to degradation by the effects of light and the properties of which are improved by the incorporation therein of a compound of formula I include natural and synthetic polymeric materials, for instance natural and synthetic rubbers, the latter including, for example, homo-, co- and terpolymers of acrylonitrile, butadiene and sytrene.

Specific synthetic polymers include polyvinyl chloride and vinyl chloride co-polymers, polyvinyl acetate as well as condensation polymers derived from ether, ester (derived from carboxylic, sulphonic or carbonic acids) amide or urethane compounds; polyvinyl acetals; polyacrylates such as polymers and copolymers of methyl acrylate, ethyl acrylate, methyl methacrylate and ethyl methacrylate; polyamides; urea-formaldehyde and melamine - formaldehyde resinsl cellulose plastics such as cellulose acetate, cellulose butyrate and cellulose nitrate. Certain of these polymers can, for instance, form the basis of surface coating media such as paints and lacquers having an oil or resin base, such as an alkyd or polyamide resin.

The amount of the compound of formula I which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol ethanol or acetone to powdered polymer and the whole mixed intimately in a mixer; and the solvent subsequently removed. As a further alternative the compound of formula I may be added to the polymer during the preparation of the latter, for instance at the latex stage of polymer production, to provide pre-stabilised polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass-fibres, kaolin and talc.

The present invention therefore includes binary, tertiary and multi-component compositions containing, as stabiliser, a compound of formula I together with one or more functional additives for polymers.

Examples of suitable antioxidants are those of the hindered phenol type such as those selected from the following groups:

(1) Phenolic compounds having the general formula

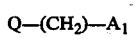

wherein
Q is

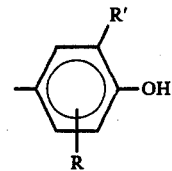

$A_1$ is $-CR(COOR'')_2$

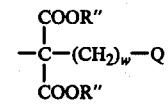

R is hydrogen or lower alkyl
R' is lower alkyl
R'' is alkyl group having from 6 - 24 carbon atoms
W is an integer from 0 to 4.

Illustrative examples of the compounds shown above are:
di-n-octadecyl-α-(3,5-di-t-butyl-4-hydroxy-benzyl)-malonate
di-n-octadecyl-α-(3-t-butyl-4-hydroxy-5-methyl-benzyl)malonate   di-n-octadecyl-α,α'bis-(3-t-butyl-4-hydroxy-5-methyl-benzyl)malonate.

(2) Phenolic compounds having the general formula
Q-R'''

Illustrative examples of the compounds shown above are:
2,6-di-t-butyl-p-cresol
2-methyl-4,6-di-t-butylphenol and the like
2,6-di-Octadecyl-p-cresol (3) Phenolic compounds having the formula

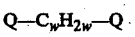

Illustrative examples of the compounds shown are:
2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(2-t-methylcyclohexyl)-4-methylphenol]
2,2'-methylene-bis(3-t-butyl-5-ethylphenol)
4,4'-methylene-bis(3,5-di-t-butylphenol)
4,4'-methylene-bis(3-t-butyl-5-methylphenol)
2,2'-methylene-bis(3-t-butyl-5-methylphenol) and the like.

(4) Phenolic compounds having the formula:

Illustrative examples of such compounds are:
2,5-di-t-butylhydroquinone
2,6-di-t-butylhydroquinone
2,5-di-t-butyl-4-hydroxyanisole (5) Phenolic compounds having the formula:

Illustrative examples of such compounds are:
4,4'-thiobis-(2-t-butyl-5-methylphenol)

4,4'-thiobis-(2-t-butyl-6-methylphenol)
2,2'-thiobis-(6-t-butyl-4-methylphenol)
4,4'-thiobis-(2-methyl-5-t-butylphenol)
(6) Phenolic compounds having the formula

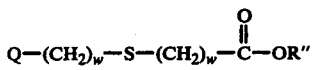

Illustrative examples of such compounds are:
octadecyl-(3,5-dimethyl-4-hydroxybenzylthio)-acetate
dodecyl-(3,5-di-t-butyl-4-hyroxybenzylthio)-propionate
(7) phenolic compounds having the formula

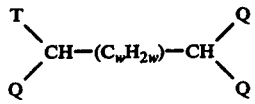

wherein T is hydrogen
R or Q as defined above.
Illustrative examples of such compounds are:
1,1,3-tris(3,5-dimethyl-4-hydroxyphenyl)-propane
1,1,3-tris(5-t-butyl-4-hydroxy-2-methylphenyl)-butane
1,1,5,5-tetrakis-(3'-t-butyl-4'-hydroxy-6'-methylphenyl)-n-pentane
(8) Phenolic compounds having the formula:

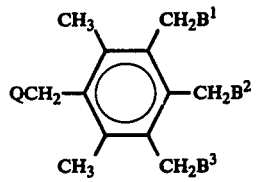

wherein $B^1$, $B^2$ and $B^3$ are hydrogen, methyl or Q, provided that when $B^1$ and $B^3$ are Q then $B^2$ is hydrogen or methyl and when $B^2$ is Q then $B^1$ and $B^3$ are hydrogen or methyl.
Illustrative examples of such compounds are:
1,4-di(3,5-di-t-butyl-4-hydroxybenzyl)-2,3,5,6-tetramethylbenzene
1,3,5-tri(3,5-di-t-butyl-4-hydroxybenzyl)-2,4,6-trimethylbenzene
(9) Phenolic compounds having the formula

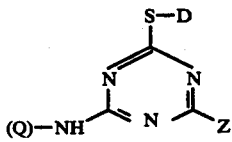

wherein
Z is NHQ, —S—D— or —O—Q
D is alkyl group having from 6 - 12 carbon atoms or —($C_wH_{2w}$)—S—R"
Illustrative examples of such compounds are:
2,4-bis-(n-octylthio)-6-(3,5-di-t-butyl-4-hydroxyaniline)-1,3,5-triazine
6-(4-hydroxy-3-methyl-5-t-butylanilino)-2,4-bis-(n-octyl-thio)-1,3,5-triazine
6(4-hydroxy-3,5-dimethylanilino)-2,4-bis-(n-octylthio)-1,3,5-triazine 6-(4-hydroxy-3,5-di-t-butylanilino)-2,4-bis-(n-octylthio)-1,3,5-triazine
6-(4-hydroxy-3,5-di-t-butylanilino)-4-(4-hydroxy-3,5-di-t-butylphenoxy)-2-(n-octylthio)1,3,5-triazine
2,4-bis(4-hydroxy-3,5-di-t-butylanilino)-6-(n-octylthio)-1,3,5-triazine
(10) Phenolic compounds having the formula:

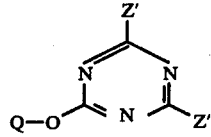

wherein Z' is —O—Q, —S—D or —S—($C_2H_{2w}$)—SD.
Illustrative examples of such compounds are:
2,3-bis-(3,5-di-t-butyl-4-hydroxyphenoxy)-6-(n-octylthio)-1,3,5-triazine
2,4,6-tris-(4-hydroxy-3,5-di-t-butylphenoxy)-1,3,5-triazine
6-(4-hydroxy-3,5-di-t-butylphenoxy)-2,4-bis-(n-octylthioethylthio)-1,3,5-triazine
6-(4-hydroxy-3-methylphenoxy)-2,4-bis-(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthiopropylthio)-1,3,5-triazine
6-(4-hydroxy-3,5-di-t-butylphenoxy)-2,4-bis-(n-dodecyl-thioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine.
(11) Phenolic compounds having the formula

wherein p is an integer from 2 to 4 and R'" is a tetravalent radical selected from aliphatic hydrocarbons having from 1 to 30 carbon atoms, aliphatic mono- and di-thioethers having from 1 to 30 carbon atoms, aliphatic mono- and diethers having from 1 to 30 carbon atoms and z is an integer from 0 to 6.
Illustrative examples of such compounds are

SUB-CLASS I n-Octadecyl-3-(3,5-di-t-butyl-4-hydroxyphenyl)-propionate n-Octadecyl-2-(3,5di-t-butyl-4-hydroxyphenyl)-acetate
n-Octadecyl-3,5-di-t-butyl-4-hydroxybenzoate
n-Hexyl-3,5-di-t-butyl-4-hydroxyphenylbenzoate n-Dodecyl-3,5-di-t-butyl-4-hydroxyphenylbenzoate
Neo-dodecyl-3-(3,5-di-t-butyl-4-hydroxyphenyl)propionate
Dodecyl-β-(3,5-di-t-butyl-4-hydroxyphenyl)propionate
Ethyl-α-(4-hydroxy-3,5-di-t-butylphenyl)-isobutyrate
Octadecyl-α-(4-hydroxy-3,5-di-t-butylphenyl)-isobutyrate
Octadecyl-α-(4-hydroxy-3,5-di-t-butylphenyl)-propionate

SUB-CLASS II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-Thiodiethanol bis(3,5-di-t-butyl-4-hydroxyphenyl)acetate
Diethyl glycol bis-[3,5-di-t-butyl-4-hydroxyphenyl)propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxythenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate

SUB-CLASS III 1,2-propylene glycol bis-[3-(3,5-di-t-butyl-4-hydroxyphenyl)propionate]
Ethylene glycol bis-[3-(3,5-di-t-butyl-4-hydroxyphenyl)propionate]
Neopentylglycol bis-[3-(3,5-di-t-butyl-4-hydroxyphenyl)propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]
1,2,3-butanetriol tris-[3-(3,5-di-t-butyl-4-hydroxyphenyl)propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl)propionate]

(12) Phenolic compounds having the formula

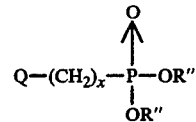

where x is an integer of 1 or 2.

Illustrative examples of such compounds are
Di-n-octadecyl 3,5-di-t-butyl-4-hydroxybenzyl-phosphonate
Di-n-octadecyl 3-t-butyl-4-hydroxy-5-methylbenzyl-phosphonate
Di-n-octadecyl 1-(3,5-di-t-butyl-4-hydroxyphenyl)-ethanephosphonate
Di-n-tetradecyl 3,5-di-t-butyl-4-hydroxybenzylphosphonate
Di-n-hexydecyl 3,5-di-t-butyl-4-hydroxybenzylphosphonate
Di-n-docosyl-3,5-di-t-butyl-4-hydroxybenzylphosphonate
Di-n-octadecyl 3,5-t-butyl-4-hydroxybenzylphosphonate.

(13) Phenolic compounds having the formula

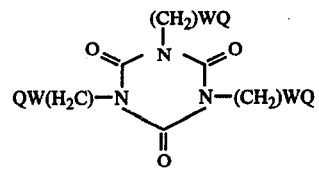

wherein W and Q are defined above.

Illustrative examples of such compounds are:
tris-(3,5-di-t-butyl-4-hydroxybenzyl)isocyanurate
tris-(3-t-butyl-4-hydroxy-5-methylbenzyl)isocyanurate.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:
phenyl-1-naphthylamine
phenyl-2-naphthylamine
N,N'-diphenyl-p-phenyldiamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and
polymerised 2,2,4-trimethyl-1,2-dihydroquinoline.

Ultraviolet absorbers and light protectants include
(a) 2-(2'-hydroxyphenyl)benzotriazoles, for instance 5'-methyl; 3',5'-di-t-butyl; 5'-t-butyl; 5-chloro-3',5'-di-t-butyl; 5-chloro-3'-t-butyl-5'-methyl; 3'-sec.butyl-5'-tert.butyl; 3'-[α-methylbenzyl]-5'-methyl-; 3'-[α-methylbenzyl]-5'-methyl-5-chloro-; 4'-octoxy-; 3',5'-di-t-amyl; 3'-methyl-5'-carbamethoxyethyl; 5-chloro3',5'-di-t-amyl derivatives.
(b) 2,4-bis-(2'-hydroxyphenyl)-6-alkyl-S-triazines, for instance the 6-ethyl or 6-undecyl derivatives.
(c) 2-hydroxybenzophenones, for instance the 4-hydroxy, 4-methoxy, 4-octoxy-, 4-decyloxy-, 4- dodecyloxy-, 4,2′4′-trihydroxy or 2-hydroxy-4,4′-dimethoxy derivatives.

(d) 1,3-Bis(2′-hydroxybenzoyl)-benzenes for instance, 1,3-bis-(2-hydroxy-4′-hexyloxybenzoly)benzene 1,3-bis(2′-hydroxy-4′-octoxybenzolyl)benzene 1,3-bis-(2′-hydroxy-4′-dodecyloxybenzoyl)benzene (e) Aryl esters from optionally substituted benzoic acids such as phenylsalicylate, octylphenylsalicylate, dibenzoyl resorcinol, bis-(4-tert.butylbenzoyl) resorcinol, benzoylresorcinol and 3,5-di-tert.butyl-4-hydroxy-benzoic acid-2,4-di-tert.butyl phenyl ester and -octadecyl ester and -2-methyl-4,6-di-tert.butyl phenyl ester.

(f) Acrylates, for instance α-Cyano-β,β-diphenylacrylic acid ethyl- or iso-octyl ester, β-carbomethoxy-cinnamic acid, methyl- or butyl ester and N-(β-carbomethoxy-vinyl)-2-methane indoline.

(g) Nickel compounds such as nickel complexes of 2,2′-thio-bis-(4-tert.octylphenol), for instance the 1:1 and 1:2 complexes, optionally having other ligands such as n-butylamine, triethanolamine or N-cyclohexyl-diethanolamine; nickel complexes of bis-(4-tert.octylphenyl) sulphone such as the 2:1 complex, optionally having other ligands such as 2-ethylcaproic acid; nickel dibutyl dithiocarbamates; nickel salts of 4-hydroxy-3,5-di-tert.butyl-benzyl-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and (h) Oxalic acid diamides, for instance 4,4′-dioctyloxyaoxanilide 2,2′-dioctyloxy-5,5′-di-tert.butyl-oxanilide 2,2′-di-dodecyloxy-5,5′-di-tert.butyl oxanilide 2-ethoxy-5-tertiarybutyl-2′-ethyl-oxanilide 2-ethoxy-2′-ethyl-oxanilide mixtures of o- and p-methoxy and ethoxy-di-substituted oxanilides and the compound of formula:

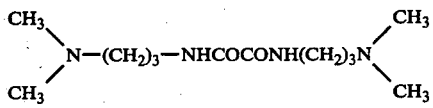

Phosphite stabilisers include triphenyl phosphite diphenylalky phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert.butylphenyl)phosphite.

Peroxide-decomposing compounds for polyolefins include esters of β-thiodiproponic acids, for instance the lauryl-, stearyl-, myristyl- or tridecyl esters, salts of mercaptobenzimidazoles such as the zinc salt and diphenylthiourca.

Suitable polyamide stabilisers include copper salts in combinations with iodides and/or further phosphorus compounds and salts of bivalent manganese.

Basic co-stablisers are, for example, polyvinylpyrrolidone, melamine, benzoguanamine, triallyl cyanurate, dicyandiamide, urea derivatives hydrazine derivatives, amines, polyamides, polyurethanes, alkali and alkaline earch salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, any further additive is advantageously employed in a proportion within the range of from 0.01% to 5% by weight, based on the weight of untreated organic materials.

In combination with an antioxidant, for instance one of the hindered phenol type, suitable for use in inhibiting oxidative deterioration of polyolefines, the compounds of formula I provide extremely effective all round stabilising packages for polyolefines.

Some Examples will now be given. Parts and percentages shown therein are by weight unless otherwise stated.

EXAMPLE 1

112 parts by weight of triethylphosphonoacetate were added with stirring over 30 minutes to a suspension of 24 parts by weight of sodium hydride (50% dispersion in oil) in 500 parts by volume of dry dioxan. The reaction temperature being 20°–30° C. The resulting solution was stirred at room temperature for one hour when a solution of 77.5 parts by weight of 2,2,6,6-tetramethylpiperidin-4-one in 100 parts by volume of dry dioxan was added over 15 minutes with stirring. The solution was stirred at room temperature for one hour and then heated to reflux for a further one hour.

After then cooling to room temperature, the suspension was poured into 1000 parts by volume of water and extracted with 6 × 100 parts by volume of ether, the combined ether extracts were dried and the ether removed by distillation at 12 mm Hg and a bath temperature of 100° C. max.

The residual oil was distilled to give 90 parts by weight (80% of theory yield) of pure ethyl(2,2,6,6-tetramethyl-piperidinylidene-4)acetate, boiling at 136° C/12 mm Hg and having the following elemental analysis by weight.

|  | C | H | N |
|---|---|---|---|
| Found | 69.02 | 10.28 | 6.04% |
| Required for $C_{13}H_{23}NO_2$ | 69.29 | 10.29 | 6.22% |

EXAMPLE 2

4.5 parts by weight of ethyl(2,2,6,6-tetramethyl-piperidinylidene-4)acetate, 3.2 parts by weight of 2,2,6,6-tetramethylpiperidin-4-ol and 0.4 parts by weight of lithium amide were heated for 3 hours at 125° C/80 mm Hg, then at 150° C/12 mm Hg for one hour. The resulting mass was cooled and triturated with 100 parts by volume of water to give a while solid which was collected by filtration. This was dissolved in 50 parts by volume of ethyl alcohol and then reprecipitated by the addition of 200 parts by volume of water, the solid was collected by filtration and dried at 60° C/0.1 mm Hg for two hours to give pure (2′, 2′, 6′, 6′-tetramethylpiperidinyl-4) (2,2,6,6-tetramethyl-piperidinylidene-4)acetate as a viscous oil having the following elemental anaylsis by weight.

|  | C | H | N |
|---|---|---|---|
| Found | 71.18 | 10.69 | 8.46% |
| Required for $C_{20}H_{36}N_2O_2$ | 71.38 | 10.78 | 8.32% |

EXAMPLE 3

13.5 parts by weight of ethyl(2,2,6,6-tetramethylpiperidinylidene-4)acetate, 10 parts by weight of cyclohexanol and 1.2 parts by weight of lithium amide were heated at 160° C./760 /mm Hg for 20 minutes, then at 160° C./80 mm Hg for a futher ten minutes. The resulting mass was cooled and dissolved in 200 parts by volume of ether, which was then washed with 2 × 50 parts by volume of water. The ether was then dried over magnesium sulphate and removed by distillation at 100° C./12 mm Hg max. and the residual oil was purified by distillation to give cyclohexyl (2,2,6,6-tetramethylpiperidinylidene-4) acetate, boiling at 125° C/0.6 mm Hg, and having the following elemental analysis by weight.

|  | C | H | N |
|---|---|---|---|
| Found | 73.02 | 10.19 | 4.80% |
| Required for $C_{17}H_{29}NO_2$ | 73.07 | 10.46 | 5.01% |

EXAMPLE 4

31.6 Parts by weight of ethyl(2,2,6,6-tetramethylpiperidinylidene-4) acetate, 17 parts by volume of 98% formic acid and 13 parts by volume of aqueous formaldehyde (36%) were heated at 100° C., with stirring, for 5 hours. The solution was then cooled, basified with excess of 46% aqueous sodium hydroxide and the oil was extracted with ether (3 × 100 parts by volume). The combined ether extracts were dried, the ether removed by evaporation at reduced pressure and the residual oil was purified by distillation, to give 18.6 parts by weight of ethyl (1,2,2,6,6-pentamethylpiperidinylidene-4) acetate boiling at 151°-2° C./12 mm. Hg and having the following elemental analysis by weight:

|  | C | H | N |
|---|---|---|---|
| Found | 70.34 | 10.21 | 6.08% |
| Required for $C_{14}H_{25}NO_2$ | 70.25 | 10.53 | 5.83% |

EXAMPLE 5

A mixture of 11.3 parts by weight of ethyl (2,2,6,6-tetramethylpiperidinylidene-4) acetate, 7.8 parts by weight of n-octanol and 1 part by weight of lithium amide was heated at 160° C for 30 minutes and at 100° C/12 mm. Hg for a further 15 minutes. The residual oil was cooled and poured into water the product was isolated by extraction with diethyl ether (6 × 50 parts by volume) followed by drying (over magnesium sulphate) and evaporation of the solvent. The product was purified by distillation to give n-octyl (2,2,6,6-tetramethylpiperidinylidene-4) acetate boiling at 140°-2° C/0.6 mm.Hg, and having the following elemental analysis by weight.

|  | C | H | N |
|---|---|---|---|
| Found | 73.49 | 11.69 | 4.60% |
| Required for $C_{19}H_{35}NO_2$ | 73.74 | 11.40 | 4.53% |

EXAMPLE 6

A mixture of 3.1 parts by weight ethane diol, 33.8 parts by weight of ethyl (2,2,6,6-tetramethylpiperidinylidene-4) acetate and 1 part by weight of lithium amide was treated as in Example 5 to give ethane-1,2-di[(2,2,6,6-tetramethylpiperidinylidene-4)acetate] boiling at 202°-4° C/0.8 mm Hg, and having the following elemental analysis by weight:

|  |  |  |  |
|---|---|---|---|
| Found | 68.72 | 9.80 | 6.70% |
| Required for $C_{24}H_{40}N_2O_4$ | 68.54 | 9.59 | 6.66% |

EXAMPLE 7

A mixture of 11.3 parts by weight of ethyl(2,2,6,6-tetramethylpiperidinylidene-4)acetate, 5 parts by weight of cyclohexylamine and 0.5 parts by weight of sodium methoxide was heated with stirring at 160° C for 1 hour. The reaction mixture was then cooled and triturated with water, and the resulting white solid was collected by filtration. This was re-crystallized from 80 parts by volume of petroleum ether (boiling range 60°-80° C) to give N-cyclohexyl-(2,2,6,6-tetramethylpiperidinylidene-4)acetamide, melting at 105°-6° C, and having the following elemental analysis by weight:

|  | C | H | N |
|---|---|---|---|
| Found | 73.38 | 10.84 | 10.21% |
| Required for $C_{17}H_{30}N_2O$ | 73.33 | 10.86 | 10.06% |

EXAMPLE 8

A mixture of 11.3 parts by weight of ethyl (2,2,6,6-tetramethylpiperidinylidene-4)acetate, 13.5 parts by weight of n-octadecanol, and 0.5 parts by weight of lithium amide was treated as in Example 5 to give n-octadecyl(2,2,6,6-tetramethylpiperidinylidene-4)acetate boiling at 236°-8° C./0.5mm and having the following elemental analysis by weight:

|  | C | H | N |
|---|---|---|---|
| Found | 77.72 | 12.31 | 3.32% |
| Required for $C_{29}H_{55}NO_2$ | 77.45 | 12.33 | 3.11% |

EXAMPLE 9

A mixture of 22.5 parts by weight of ethyl(2,2,6,6-tetramethylpiperidinylidene-4)acetate, 4.5 parts by weight of butane-1,4-diol and 1 part by weight of lithium amide was treated as in Example 5 to give butane-1,4-di[(2',2',6',6'-tetramethylpiperidinylidene-4'-)acetate], boiling at 220°-4° C./0.5mm and having the following elemental analysis by weight:

|  | C | H | N |
|---|---|---|---|
| Found | 69.61 | 10.20 | 6.11% |
| Required for $C_{26}H_{44}N_2O_4$ | 69.61 | 9.90 | 6.24% |

EXAMPLE 10

A mixture of 11.9 parts by weight ethyl(1,2,2,6,6-pentamethylpiperidinylidene-4)acetate, 6.0 parts by weight of cyclohexanol and 0.5 parts by weight of lithium amide were treated as in Example 5 to give cyclohexyl(1,2,2,6,6-pentamethylpiperidinylidene-4)acetate, boiling at 155°–6° C./0.8mm, and having the following elemental analysis by weight:

|  | C | H | N |
|---|---|---|---|
| Found | 73.70 | 10.66 | 4.92% |
| Required for $C_{18}H_{31}NO_2$ | 73.67 | 10.65 | 4.77% |

EXAMPLE 11

A mixture of 11.9 parts by weight of ethyl(1,2,2,6,6-pentamethylpiperidinylidene-4)acetate, 7.8 parts by weight of n-octanol and 0.5 parts by weight of lithium amide were treated as in Example 5 to give n-octyl(1,2,2,6,6-pentamethylpiperidinylidene-4)acetate, boiling at 158°–160° C./0.9mm and having the following elemental analysis by weight:

|  | C | H | N |
|---|---|---|---|
| Found | 74.82 | 11.67 | 4.43% |
| Required for $C_{20}H_{37}NO_2$ | 74.25 | 11.53 | 4.33% |

EXAMPLE 12

A mixture of 35.9 parts by weight of ethyl(1,2,2,6,6-pentamethylpiperidinylidene-4)acetate, 3.1 parts by weight of ethane-1,2-diol and 0.5 parts by weight of lithium amide were treated as in Example 5 to give ethane-1,2-di[(1',2',2',6',6'-pentamethylpiperidinylidene-4') acetate], boiling at 215°–8° C./0.8mm, and having the following elemental analysis by weight:

|  | C | H | N |
|---|---|---|---|
| Found | 70.47 | 10.03 | 6.31% |
| Required for $C_{26}H_{44}N_2O_4$ | 69.61 | 9.90 | 6.24% |

EXAMPLE 13

A mixture of 11.3 parts by weight of ethyl(2,2,6,6-tetramethylpiperidinylidene-4)acetate, 10.1 parts by weight of n-hexylamine and 2.7 parts by weight of sodium methoxide were treated as in Example 5 to give N-(n-hexyl)(2,2,6,6-tetramethylpiperidinylidene-4acetamide, boiling at 180°–2° C./0.9mm, and having the following elemental analysis by weight:

|  | C | H | N |
|---|---|---|---|
| Found | 72.87 | 11.50 | 9.71% |
| Required for $C_{17}H_{32}N_2O$ | 72.81 | 11.50 | 9.99% |

EXAMPLE 14

A mixture of 11.3 parts by weight of ethyl(2,2,6,6-tetramethylpiperidinylidene-4)acetate, 10.8 parts by weight of n-octadecylamine and 2.7 parts by weight of sodium methoxide were treated as in Example 7 to give a white solid, which by recrystallisation from petroleum ether (boiling range 40°–60° C.) gave pure N-(n-octadecyl) (2,2,6,6-tetramethylpiperidinylidene-4) acetamide melting at 56° C., and having the following elemental analysis by weight:

|  | C | H | N |
|---|---|---|---|
| Found | 77.51 | 12.53 | 6.01% |
| Required for $C_{29}H_{56}N_2O$ | 77.62 | 12.58 | 6.24% |

EXAMPLE 15

A mixture of 138 parts by weight ethyl(2,2,6,6-tetramethylpiperidinylidene-4)acetate, 11.2 parts by weight of n-dodecylamine, and 1 part by weight of sodium methoxide were treated as in Example 5 to give 12.3 parts by weight of N-(ndodecyl)(2,2,6,6-tetramethyl-yl-piperidinylidene-4) acetamide, boiling at 215°–218° C./0.8mm, and having the following elemental analysis by weight:

|  | C | H | N |
|---|---|---|---|
| Found | 75.66 | 12.27 | 7.62% |
| Required for $C_{23}H_{44}N_2O$ | 75.77 | 12.16 | 7.68% |

EXAMPLE 16

A mixture of 11.3 parts by weight of ethyl(2,2,6,6-tetramethylpiperidinylidene-4)acetate, 5.4 parts by weight of benzylamine and 2.5 parts by weight of sodium methoxide were treated as in Example 5 to give N-benzyl(2,2,6,6-tetramethylpiperidinylidene-4)-acetamide, boiling at 186°–90° C./0.7mm and having the following elemental analysis by weight:

|  | C | H | N |
|---|---|---|---|
| Found | 75.33 | 9.14 | 9.63% |
| Required for $C_{18}H_{26}N_2O$ | 75.48 | 9.15 | 9.78% |

EXAMPLE 17

A mixture of 26.9 parts by weight of ethyl(2,2,6,6-tetramethyliperidinylidene-4)acetate, 3.0 parts by weight of ethane-1,2-diamine and 5.4 parts by weight of sodium methoxide were treated as in Example 7 to give a white solid, which by recrystallisation from ethyl acetate gave pure N,N'-Di[(2,2,6,6-tetramethylpiperidinylidene-4) acetyl]ethylene diamine, melting at 170°–2° C. and having the following elemental analysis by weight:

|  | C | H | N |
|---|---|---|---|
| Found | 68.63 | 10.33 | 13.57% |
| Required for $C_{24}H_{42}N_4O_2$ | 68.86 | 10.11 | 13.38% |

EXAMPLE 18

A solution of 10 parts by weight of ethyl (1,2,2,6,6-pentamethylpiperidinylidene-4)acetate in 100 parts by volume of methanol saturated with ammonia was allowed to stand at room temperature for 30 days. The methanol was then removed by distillation and the residual solid recrystallised from cyclohexane to give pure (1,2,2,6,6-pentamethylpiperidinylidene-4)acetamide, melting at 103° C., and having the following elemental analysis by weight:

|  | C | H | N |
|---|---|---|---|
| Found | 68.80 | 10.60 | 13.13 |
| Required for C$_{12}$H$_{22}$N$_2$O | 68.53 | 10.54 | 13.32 |

EXAMPLE 19

A mixture of 11.9 parts by weight of ethyl(1,2,2,6,6-pentamethylpiperidinylidene-4)acetate, 5.0 parts by weight of n-hexylamine and 2.7 parts by weight of sodium methoxide were treated as in Example 5 to give 9.3 parts by weight of N-(n-hexyl)(1,2,2,6,6-pentamethylpiperidinylidene-4)acetamide, boiling at 166°-70°C./0.6mm and having the following elemental analysis by weight:

|  | C | H | N |
|---|---|---|---|
| Found | 73.61 | 11.67 | 9.36% |
| Required for C$_{18}$H$_{34}$N$_2$O | 73.42 | 11.64 | 9.51% |

EXAMPLE 20

A mixture of 11.9 parts by weight of ethyl(1,2,2,6,6-pentamethylpiperidinylidene-4)acetate, 5.0 parts by weight of cyclohexylamine and 0.5 part by weight of sodium methoxide were treated as in Example 7 to give 9.5 parts by weight of N-cyclohexyl(1,2,2,6,6-pentamethylpiperidinylidene-4) acetamide, melting at 157°-8° C. and having the following elemental analysis by weight:

|  | C | H | N |
|---|---|---|---|
| Found | 74.15 | 11.03 | 9.31% |
| Required for C$_{18}$H$_{32}$N$_2$O | 73.92 | 11.03 | 9.58% |

Example 21

A mixture of 26.7 parts by weight of ethyl(1,2,2,6,6-pentamethylpiperidinylidene-4)acetate, 3.0 parts by weight of ethylenediamine and 2.7 parts by weight of sodium methoxide were treated as in Example 7. The white solid obtained was recrystallised from ethyl alcohol to give Di[(1,2,2,6,6-pentamethylpiperidinylidene-4)acetyl]ethylene diamine, melting at 189°-90° C., and having the following elemental analysis by weight:

|  | C | H | N |
|---|---|---|---|
| Found | 70.07 | 10.33 | 12.38% |
| Required for C$_{26}$H$_{46}$N$_4$O$_2$ | 69.91 | 10.38 | 12.54% |

EXAMPLE 22 a mixture of 19.3 parts by weight of ethyl(1,2,2,6,6-pentamethylpiperidinylidene-4)acetate, 3.5 parts by weight of hexane-1,6-diamine and 3.6 parts by weight of sodium methoxide were treated as in Example 7. The white solid product was recrystallised from ethyl acetate to give Di[(1,2,2,6,6-pentamethylpiperidinylidene-4)acetyl]hexane1,6-diamine, melting at 134°-5° C., and having the following elemental analyis by weight:

|  | C | H | N |
|---|---|---|---|
| Found | 71.83 | 10.85 | 11.18% |
| Required for C$_{30}$H$_{54}$N$_4$O$_2$ | 71.67 | 10.83 | 11.14% |

EXAMPLES 23 to 28

38 parts of polypropylene were homogenised with 0.076 parts of n-octadecyl-β-(4'-hydroxy-3',5'-t-butylphenyl) propionate in a kneading machine over a period of 3 minutes. 0.19 part of the product of Example 1 was then added and homogenisation continued for another 7 minutes.

The homogenised mixture was removed from the kneader and pressed to a thickness of from 2 to 3 mm. in a press.

9 parts of the polypropylene mixture were then charged into a second press in which the press-plates were protected by aluminium foil having a thickness of 0.1 mm. The press was closed and, for 2 minutes, no pressure was applied. The pressure was then increased up to a maximum of 12 tons and this pressure held for 6 minutes, the temperature of the press being 260° C. The pressure was released and the material (0.3 mm thick) was cooled under running water.

This material was cut into from 3 to 5 pieces of 35 × 35 mm section and re-changed to the press. The press was closed and no pressure was applied for 2 minutes. Over another 2 minutes the pressure was increased to 8 tons, the press temperature being 260° C. This pressure was maintained for 2 minutes and then the pressure released. The polypropylene foil of 0.1 mm thickness was removed and tempered immediately in a circulating air oven maintained at 150° C over a period of 60 minutes.

A section measuring 44 × 100 mm was separated from the 0.1 mm tempered polypropylene foil and exposed to light irradiation in a fademeter device consisting of a circular bank of 28 alternating sunlight and blacklight lamps. The sunlight lamps were 2 feet long, 20-watt fluorescent lamps characterised by a peak emission of 3100 Angstrom units; the blacklight lamps were 2 feet long, 20-watt ultraviolet lamps characterised by a peak emission of 3,500 Angstrom units. The sample was rotated concentrically about the bank of lamps so that the radiation therefrom was uniformly distributed over the section under test.

The exposed sample was examined periodically, when portions of it were removed for tensile testing and the time (T) was determined after which the elongation of the sample, had decreased to 50% of the initial elongation.

The results obtained are set out in the Table which includes results relating to a control experiment and also to an experiment replacing the product of Example I by that of Example 3,4,7,10 or 17.

TABLE

| Example | Additive | T for component T for control |
|---|---|---|
| — | none (control) | 1 |
| 23 | Ethyl(2,2,6,6-tetramethyl-piperidinylidene-4)acetate | 2.7 |
| 24 | Cyclohexyl(2,2,6,6-tetra-methylpiperidinylidene-4) acetate | 3.4 |
| 25 | Cyclohexyl(1,2,2,6,6-penta-methylpiperidinylidene-4) acetate | 4.3 |

TABLE-continued

| Example | Additive | T for component T for control |
|---|---|---|
| 26 | Ethyl(1,2,2,6,6-pentamethyl-piperidinylidene-4)acetate | 4.1 |
| 27 | N-Cyclohexyl(2,2,6,6-tetra-methylpiperidinylidene-4)acetamide | 3.8 |
| 28 | N,N'-Di[2,2,6,6-tetramethyl-piperidinylidene-4)acetyl]-1,2-ethanediamine | 2.9 |

EXAMPLE 29

A solution of 60 parts by weight of ethyl(2,2,6,6tetramethylpiperidinylidene-4)acetate in 400 parts by volume of 18% hydrochloric acid were heated at reflux for 4 hours. The volume of the solution was reduced to 50 parts by distillation under reduced pressure, and the precipitate collected by filtration. Thus was obtained 54 parts (82% of theory yield) of (2,2,6,6-tetramethylpiperidinylidene-4) acetic acid as hydrochloride salt having the following elemental analysis by weight:

|  | C | H | N | Cl |
|---|---|---|---|---|
| Found | 56.80 | 8.55 | 15.26 | 5.85% |
| Required for $C_{11}H_{20}ClNO_2$ | 56.50 | 8.56 | 15.20 | 5.99% |

I claim:
1. A compound of the formula I

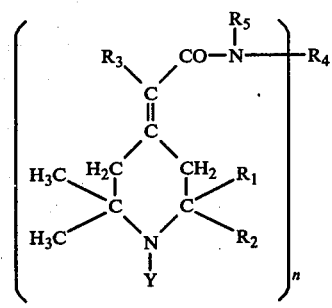

wherein
$n$ is 1, 2, 3 or 4,
Y is hydrogen or a straight- or branched alkyl group having from 1 to 12 carbon atoms, an alkenyl group having from 3 to 12 carbon atoms or an aralkyl group having from 7 to 12 carbon atoms
$R_1$ and $R_2$ are the same or different and each is a straight-or branched alkyl group having from 1 to 12 carbon atoms or $R_1$ and $R_2$, together with the carbon atom to which they are attached, form a cycloalkyl group having from 5 to 12 carbon atoms,
$R_3$ is hydrogen, a straight- or branched alkyl group having from 1 to 4 carbon atoms, an aralkyl group having from 7 to 12 carbon atoms, or a cycloalkyl group having from 5 to 6 carbon atoms
$R_4$ is a group having from 1 to 20 carbon atoms which is selected from the group consisting of
when $n$ is 1, alkyl group which is unsubstituted or substituted, with alkyl, alkoxy, thioalkyl, halogen, phenyl or alkyl or chlorine substituted benzyl; alkenyl group which is unsubstituted or substituted with alkyl or phenyl; alkynyl group; aryl group which is unsubstituted or substituted with alkyl or alkoxy; cycloalkyl group which is unsubstituted or substituted with alkyl, alkoxy, or halogen; hydrogen or the structure:

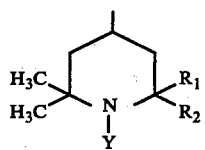

wherein Y, $R_1$ and $R_2$ are as defined above,
when $n$ is 2, alkylene group which is unsubstituted or substituted with alkyl and which may be oxygen or sulfur interrupted or possess an unsaturation; cycloalkylene group; arylene;
when $n$ is 3, a trivalent alkyl group of 3 to 15 carbons which is saturated or unsaturated; a trivalent cycloalkyl group of 5 to 15 carbons; a trivalent aralkyl group of 9 to 15 carbon atoms or a trivalent aryl group of 6 to 15 carbons;
when $n$ is 4, a tetravalent alkyl group of 4 to 12 carbons which is saturated or unsaturated or a tetravalent cycloalkyl group of 5 to 12 carbons; and $R_5$ has the same significance as $R_3$ or when $n$ is 1, $R_5$ and $R_4$, together with the nitrogen atom to which they are bound form a heterocyclic group having from 4 to 10 carbon atoms and nitrogen as the only hetero atom, or $R_5$ and $R_4$, together with the nitrogen atom to which they are bound, form 1- morpholinyl group and a salt of the amine function of a compound of formula I.

2. A salt of claim 1 which is selected from the group consisting of phosphates, carbonates, sulphates, chlorides and the like, as well as organic acid salts such as acetates, stearates, maleates, citrates, tartrates, oxalates, and benzoates, and the substituted carbamic acids.

3. A compound according to claim 1 wherein Y is hydrogen or methyl.

4. A compound according to claim 3 wherein $R_1$ and $R_2$ are each methyl.

5. A compound according to claim 4 wherein $R_3$ and $R_5$ are each hydrogen.

6. A compound according to claim 5 wherein $R_4$ is an alkyl group having at least 6 carbon atoms.

7. A compound according to claim 1 wherein $n$ is 1 and $R_4$ is hydrogen, a monovalent straight- or branched alkyl group either saturated or unsaturated having from 1 to 20 carbon atoms, an alicyclic group having from 5 to 20 carbon atoms, an aryl group having from 6 to 15 carbon atoms or $R_4$ and $R_5$, together with the nitrogen atom to which they are bound form a heterocyclic group having from 4 to 10 carbon atoms.

8. A compound according to claim 1 wherein $n$ is 2 and $R_4$ is a divalent straight- or branched alkyl group either saturated or unsaturated, having from 2 to 20 carbon atoms, a divalent alicyclic group having from 5 to 20 carbon atoms, a divalent aralkyl group having from 8 to 20 carbon atoms or a divalent aryl group having from 6 to 20 carbon atoms.

9. The compound of claim 1 which is N-(in-hexyl)(2,2,6,6-tetramethylpiperidinylidene-4)acetamide.

10. The compound of claim 1 which is N-(n-octadecyl) (2,2,6,6-tetramethylpiperidinylidene-4)acetamide.

11. The compound of claim 1 which is N-(n-dodecyl) (2,2,6,6-tetramethyl-piperidinylidene-4)acetamide.

12. The compound of claim 1 which is n-benzyl (2,2,6,6-tetramethylpiperidinylidene-4)acetamide.

13. The compound according to claim 1 which is N,N'-di[(2,2,6,6-tetramethylpiperidinylidene-4)acetyl]ethylene diamine.

14. The compound according to claim 1 which is (1,2,2,6,6-pentamethylpiperidinylidene-4)acetamide.

15. The compound according to claim 1 which is N-(n-hexyl) (1,2,2,6,6-pentamethylpiperidinylidene-4)acetamide.

16. The compound according to claim 1 which is N-cyclohexyl(1,2,2,6,6-pentamethylpiperidinylidene-4)acetamide.

17. The compound according to claim 1 which is di[(1,2,2,6,6-pentamethylpiperidinylidene-4)acetate]hexane-1,6-diamine.

18. A compound according to claim 1 which is N-cyclohexyl-(2,2,6,6-tetramethyl-piperidinylidene-4)-acetamide.

19. A compound according to claim 1 which is di-[(1,1,2,2,6,6-pentamethyl-piperidinylidene-4)-acetyl]-ethylene diamine.

* * * * *